US007793902B2

United States Patent
Buchanan et al.

(10) Patent No.: US 7,793,902 B2
(45) Date of Patent: Sep. 14, 2010

(54) MEDICAL DEVICE CLAMP

(75) Inventors: Richard Buchanan, Hamburg, NY (US); Rob Colonna, Newton, MA (US)

(73) Assignee: Gaymar Industries, Inc., Orchard Park, NY (US)

( * ) Notice: Subject to any disclaimer, the term of this patent is extended or adjusted under 35 U.S.C. 154(b) by 566 days.

(21) Appl. No.: 11/821,444

(22) Filed: Jun. 22, 2007

(65) Prior Publication Data

US 2008/0277545 A1 Nov. 13, 2008

Related U.S. Application Data

(60) Provisional application No. 60/928,549, filed on May 10, 2007.

(51) Int. Cl.
| | |
|---|---|
| *A47B 96/06* | (2006.01) |
| *E04G 3/00* | (2006.01) |
| *E04G 5/06* | (2006.01) |
| *F16B 1/00* | (2006.01) |
| *G09F 7/18* | (2006.01) |
| *A47G 29/00* | (2006.01) |
| *A47K 1/00* | (2006.01) |
| *F21V 21/00* | (2006.01) |
| *F21V 35/00* | (2006.01) |

(52) U.S. Cl. ............... 248/230.1; 248/230.2; 248/218.4; 248/219.2; 248/222.13; 248/229.11; 248/229.21

(58) Field of Classification Search ... 248/230.1–230.2, 248/207, 214, 218.4, 219.2, 222.11–222.13, 248/229.11, 229.21, 231.31, 230.4, 230.3, 248/229.13
See application file for complete search history.

(56) References Cited

U.S. PATENT DOCUMENTS 164,088 A * 6/1875 Hunter .................. 248/113

(Continued)

OTHER PUBLICATIONS www.acemart.com—Mop/broom holder—May 25, 2007—one page.

*Primary Examiner*—J. Allen Shriver, II
*Assistant Examiner*—Christopher Garft
(74) *Attorney, Agent, or Firm*—Roach Brown McCarthy & Gruber, P.C.; Kevin D. McCarthy

(57) ABSTRACT

A medical instrument device interconnection system decreases the vibrational effects on a hospital pole. The medical device is contained in a case and the case has a first clamping member, a first biasing apparatus, a second clamping member, a second biasing apparatus, and a pole receiving trench. Each clamping member has a preferred position, an attachment position and a maximum tension position. In the preferred position the respective biasing members position the respective clamping member's distal end as close to each other as possible which inhibits a conventional hospital pole from entering the pole receiving trench. To obtain the maximum tension position, the person positioning the medical instrument device on the hospital pole aligns the pole receiving trench with the hospital pole so the hospital pole contacts the clamping members' exterior surface in the preferred position. The person raises the device in relation to the pole which causes the clamping members to rotate and expose the pole receiving trench. Once the hospital pole enters the pole receiving trench the respective biasing apparatus on each clamping member has the respective clamping members revert toward the preferred position. The preferred position cannot be obtained because the hospital pole in the pole receiving trench inhibits the clamping members from reverting to that position. Instead the clamping members are in the attachment position after the medical instrument device is lowered a little in relation to the hospital pole to obtain the maximum force in the attachment position. Collectively the biasing apparatuses through the clamping members in the attachment position provide more force to the hospital pole than the weight of the medical instrument device. That way the medical instrument device remains attached to the hospital pole and due to the flexible biasing apparatuses the device's vibration is suppressed while attached to the hospital pole.

18 Claims, 2 Drawing Sheets

U.S. PATENT DOCUMENTS

| | | | |
|---|---|---|---|
| 4,190,224 A * | 2/1980 | LeBlanc et al. | 248/227.3 |
| 5,169,106 A | 12/1992 | Rasmussen | |
| 5,332,184 A * | 7/1994 | Davis | 248/230.3 |
| 5,524,667 A * | 6/1996 | Potter | 137/343 |
| 5,588,166 A * | 12/1996 | Burnett | 5/503.1 |
| 5,725,185 A * | 3/1998 | Auclair | 248/74.2 |
| 5,779,207 A | 7/1998 | Danby | |
| 6,105,915 A * | 8/2000 | Naman et al. | 248/309.1 |
| 6,179,260 B1 * | 1/2001 | Ohanian | 248/229.16 |
| 6,382,576 B1 * | 5/2002 | Heimbrock | 248/227.3 |
| 2002/0084397 A1 * | 7/2002 | Ross, Jr. | 248/317 |
| 2003/0028159 A1 * | 2/2003 | Tracey et al. | 604/328 |
| 2004/0097872 A1 * | 5/2004 | Delk et al. | 604/67 |
| 2004/0153132 A1 * | 8/2004 | Cobb et al. | 607/104 |
| 2007/0073368 A1 * | 3/2007 | Cazzini et al. | 607/104 |
| 2008/0195184 A1 * | 8/2008 | Ziaimehr | 607/104 |
| 2008/0277545 A1 * | 11/2008 | Buchanan et al. | 248/218.4 |
| 2008/0281387 A1 * | 11/2008 | Buchanan et al. | 607/104 |

* cited by examiner

MEDICAL DEVICE CLAMP

CLAIM OF PRIORITY

This application claims priority to U.S. provisional patent application Ser. No. 60/928,549; filed on May 10, 2007.

FIELD OF THE INVENTION

This invention relates to clamps and more specifically to clamps used with medical instrument devices to be attached to hospital poles, which are sometimes referred to as IV poles.

BACKGROUND OF THE INVENTION

Hospital Pole Clamps Currently Used

In U.S. Pat. No. 5,779,207; Danby succinctly wrote, "Prior clamps [used to attach a medical instrument device to a hospital pole] comprise a knob or handwheel which serves to drive a threaded shaft against a pole so as to provide, in conjunction with a pole gripping anvil, a friction connection between the pole and the pump. Modifications of this basic idea have been to use scissors or a lever to multiply the force applied by the threaded shaft to the pole or gripped member so as to improve the mechanical qualities of the clamp.

Prior clamps, however, suffer from the same flaw. These clamps require an equal amount of force to be applied to remove the clamp as was required to affix the clamp to the gripped member. In a hospital setting, wherein orderlies and nurses share the responsibilities of placing and removing pumps, this flaw comes to the fore. For example, consider the situation where an orderly affixes a pump to a pole. At a time subsequent to this installation, another person, having less strength than the orderly, wishes to remove the pump. However, to satisfy himself that the pump was firmly affixed to the pole, the orderly applied a great deal of torque to the knob. Since torque equals force times distance, the person wishing to remove the pump must supply at least as much force to the knob as the orderly did when installing the pump. For a more lightly muscled person this task may prove to be daunting or impossible.

This difficulty, repeated over and over, has an effect on the efficiency of the staff as well as providing a source of additional wear on the equipment, as tools are commonly employed to loosen these clamps."

In U.S. Pat. No. 5,169,106; Rasmussen wrote, "A quick attach/release pole clamp is mounted on the side of a medical instrument case. A stationary clamp member is secured to the case and a movable clamp member slides in a slot oriented at a slight acute angle to the vertical, so that it moves toward and away from the stationary clamp member as it moves up and down the slot. A spring biases the movable clamp member toward the top of the slot so that the clamp is moved to the closed position. The user may support the instrument case in two hands while depressing the sliding clamp member to permit the clamp members to be positioned around a pole. When the pressure is released, the spring causes the clamp to close on the pole. A camming lever permits the user to provide positive latching of the clamp member from movement, and to engage an anti-rotation element with the pole. An interlock prohibits activation of the camming lever while the movable clamp member is being depressed."

Rasmussen further confirms Danby's interpretation of clamps used to attach medical instrument devices on IV poles, when he wrote, "In the hospital environment, it is often necessary to provide medical instrumentation at the patient bedside. Many surgical patients, for example, are provided at least on a temporary basis with an intravenous fluid delivery setup for infusion of fluids to prevent dehydration, to preserve electrolyte balance, or to deliver antibiotics and other medication. Frequently, intravenous delivery is provided by a fluid infusion pump or a gravity controller, both of which are electromechanical instrumentation which must be situated near the patient.

Typically, the instrument cases of these and other instrumentation used in patient care are provided with clamps for engaging a portable pole so that the instrumentation may be secured on such a pole. The typical pole clamp is located on the back of the instrument case, and is activated by turning a threaded clamping member to close the clamp on the pole. To carry out this securement step, the nurse or other user must support the instrument case with one hand, while turning the clamp knob with the other hand to effect closure. Removal of the instrument likewise requires that the instrument be supported by one hand during the step of unscrewing the clamping knob to free the instrument from the pole. While such clamping arrangements have been in use for many years, they can be awkward and time-consuming to utilize."

The medical instruments described and alluded to in the above-identified patents are small, essentially non-vibrational medical instruments. Examples of small, essentially non-vibrational medical instruments include and are not limited to a fluid warmer, a fluid infusion pump or a gravity controller. Those medical devices do not visibly vibrate or vibrate the hospital pole. Due to the lack of vibration, securing the medical instruments by a threaded shaft/gripping anvil embodiment, or a stationary/movable clamps embodiment is acceptable. It is known that the threaded shaft/gripping anvil embodiment and a stationary/movable clamps embodiment transfer any vibrational energy from the medical device to the hospital pole. Transferring vibrational energy to the hospital pole can be deleterious for reasons set forth below.

Example of Vibrational Medical Devices

Gaymar Industries, Inc. is the assignee of the present application, and has been manufacturing, selling and offering to sell inflatable blankets for a number of years. On Jun. 8, 1999, Circuit Judge Rader wrote a court decision that described Gaymar's thermal blankets. That decision can be found at 181 F.3d 1291, 1304, 50 USPQ2d 1900, 1909 (Fed. Cir. 1999) and it clearly describes the differences between Gaymar's thermal blanket and at least one competitor's. In his outstanding decision, he wrote, "Convective thermal blankets inflate to direct warm (or cool) air onto a person. Surgeons often use these blankets during and after an operation to prevent or treat hypothermia caused by surgical conditions. Hypothermia results when a patient's body temperature drops below a certain threshold. Surgery often presents the threat of hypothermia. A patient's body temperature may drop significantly during surgery because anesthesia prevents the patient's body from regulating its own temperature. Additionally, operating rooms—kept cool to accommodate the surgeon's working conditions and to reduce the spread of germs—can chill patients. Moreover, surgery often calls for administration of cool intravenous fluids at a time when the patient's body cavity is open.

A convective thermal blanket over the patient is thus necessary to prevent or treat hypothermia during and after surgery. Heated air from a warming unit inflates the blanket. Once inflated, the blanket directs heated air onto the patient through small holes (or "exit ports") in the undersurface of the blanket. With careful use, a convective blanket regulates patient temperature and prevents hypothermia"[, or in some cases hyperthermia.

Gaymar has been manufacturing such blankets] that feature an inflatable quilt-like structure. These blankets attach two sheets of the same amount of flexible, lightweight material around their periphery and at various spots along their surfaces [sometimes referred to as welds or spot welds depending on the shape of the attachment]. In operation, heated air flows onto a patient's body from holes in the undersurface of the blanket, and the blankets do not form a self-supporting or Quonset hut-like structure. Instead, [Gaymar's] blankets lie flat when inflated on a flat surface and rest substantially on a patient when in use." (Bracketed material is added or substitutes terms to make it relevant for this application.)

The convective blankets are inflated through Gaymar's Thermacare convective blowers. The Thermacare convective blower provides effective patient warming adaptable to a variety of procedures. The blower features a lightweight, portable, warm-air blower unit offering three temperature settings for the operating room/intensive care unit and four for the post anesthesia care unit. The blower also has a flexible, covered hose that is lightweight and easy to clean, and attaches easily and securely. The blowers are within a case that can be mounted on an IV pole by conventional threaded shaft/gripping anvil embodiment or a stationary/movable clamps embodiment, foot end of bed or on a portable stand. When the blowers are interconnected to the hospital poles through the conventional attachment embodiments, the blowers vibrate the hospital pole.

A Conventional Mop/Broom Holder

A conventional mop/broom holder is disclosed at www.acemart.com. The holder is constructed of steel with a single rubber cam and grips broom handles from ⅞ inch to 1¼ inches in diameter. The steel material is U shaped—a base, a left extension and a right extension. The single rubber cam is positioned on the base. In the embodiment illustrated at www.acemart.com, there is a handle opening between the single rubber cam and the left extension—obviously the opening can be positioned between the cam and right extension but it depends on the cam's orientation. In any case, the advertisement asserts using the single rubber cam and U-shaped steel member is easy. Simply push a handle up and into the opening and the rubber cam will adjust and hold the handle in place. To remove the handle, just push up and out with the handle. This single spring loaded cam device is used to secure broom handles or other non-medical devices to walls.

The mop/broom holder is a single rubber cam and U-shaped steel member that allows a broom or mop to be hung on a wall. There is no concern about vibration because the mops/brooms and the wall are stationary and do not vibrate. That means the conventional mop/broom holder does not have to be designed to control or minimize vibration, which the present invention must address.

SUMMARY OF THE INVENTION

In accordance with the invention, there is provided a medical instrument device having a case. The case has a first clamping member, a first biasing apparatus, a second clamping member, a second biasing apparatus, and a pole receiving trench. Each clamping member has a preferred position, an attachment position and a maximum tension position. In the preferred position the respective biasing members position the respective clamping member's distal end as close to each other as possible which inhibits a conventional hospital pole from entering the pole receiving trench. To obtain the maximum tension position, the person positioning the medical instrument device on the hospital pole aligns the pole receiving trench with the hospital pole so the hospital pole contacts the clamping members' exterior surface in the preferred position. The person raises the device in relation to the pole which causes the clamping members to rotate and expose the pole receiving trench. Once the hospital pole enters the pole receiving trench the respective biasing apparatus on each clamping member has the respective clamping members revert toward the preferred position. The preferred position cannot be obtained because the hospital pole in the pole receiving trench inhibits the clamping members from reverting to that position. Instead the clamping members are in the attachment position after the medical instrument device is lowered a little in relation to the hospital pole to obtain the maximum force in the attachment position. Collectively the biasing apparatuses through the clamping members in the attachment position provide more force to the hospital pole than the weight of the medical instrument device. That way the medical instrument device remains attached to the hospital pole. There is no actuatutor to depress to secure the medical instrument device to a hospital pole. There is no knob or hand wheel to adjust to secure the medical instrument device to the hospital pole. Releasing the medical instrument device from the hospital pole is accomplished by reversing the attachment process.

DETAILED DESCRIPTION OF THE INVENTION

Figure 1:
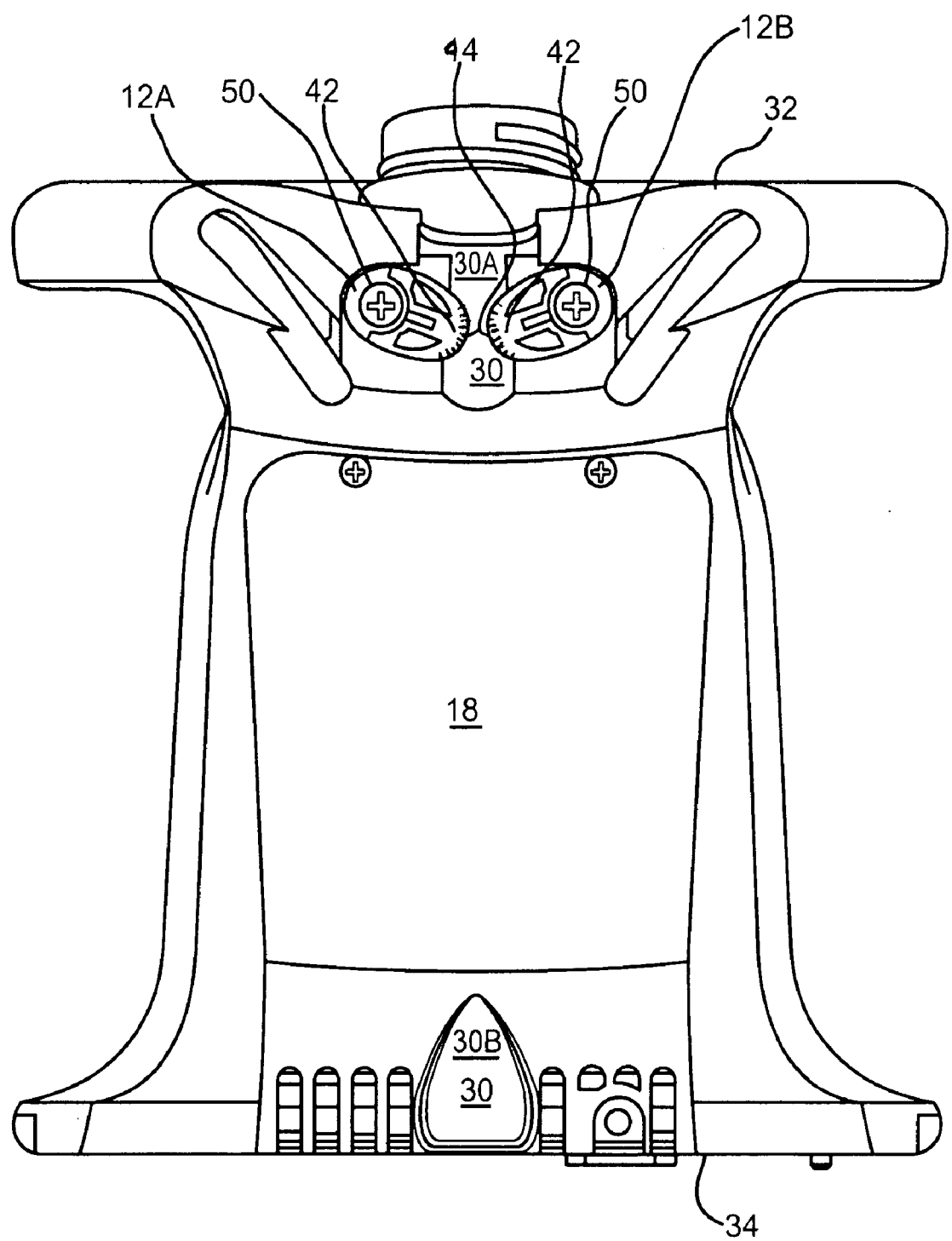
FIG. 1 illustrates a medical instrument device not attached to a hospital pole.
Figure 2:
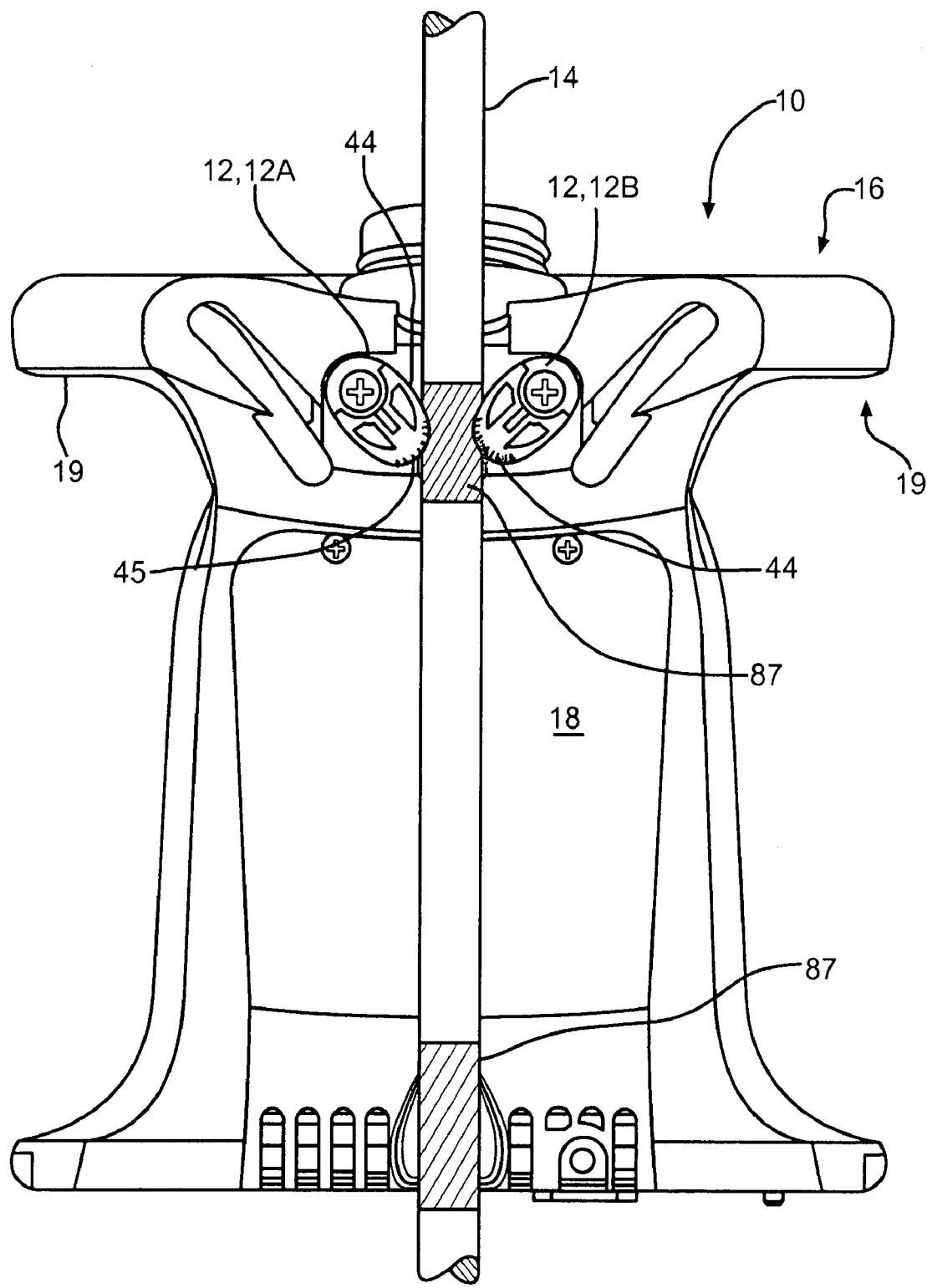
FIG. 2 illustrates an embodiment of FIG. 1 attached to a hospital pole.

A medical instrument device case 10 with a quick attach/release pole clamp system 12 constructed in accordance with the present invention is illustrated in FIGS. 1 and 2. Instrument case 10 may house any medical instrument typically utilized in a hospital environment. For example, instrument case 10 may contain an intravenous fluid pump, an intravenous fluid gravity controller, an intravenous fluid temperature controller, a blower for a convective blanket or other medical instrument which may desirably be placed adjacent a patient's bed by securement on a portable or permanent hospital pole 14.

In FIGS. 1 and 2, the case 10 encloses a blower for a convective blanket. As described above, convective blowers do vibrate which can pose problems if other medical objects are positioned on the hospital pole 14. An object of the present invention is to decrease such vibration applied to the hospital pole 14.

Instrument case 10 is provided with a main body portion 16 having a rear side 18 and a front side (not shown). Main body portion 16 has a handle 19 on its side for the person positioning the medical instrument on the hospital pole 14 to easily align, raise and lower the medical instrument in relation to the pole. The front side may typically accommodate the mechanical interface for the medical instrument device within the case 10 and may provide user controls, displays and outputs. For this invention, those controls for operating the medical device are not the subject of the present invention.

The rear side 18 has the clamp system 12 and a pole receiving/alignment trench 30. The pole receiving/alignment trench 30 is the portion of the rear side 18 that receives the hospital pole 14. Preferably, the pole receiving/alignment trench 30 does not extend along the entire rear side 18.

In a preferred embodiment, the pole receiving/alignment trench 30 is divided into at least two distinct, spaced and separate areas. The first trench area 30a is near or at the top 32 of the case 10. The second trench area 30b is near or at the bottom 34 of the case 10. The area between the first and second trench areas 30a,b on the rear side 18 is an indented and/or concave area that does not contact the pole 14. This indented/concave area is desired to decrease the contact surface area of the medical instrument device to the hospital pole 14. The decreased contact surface area can decrease the vibration effects on to the hospital pole 14 that are created when the medical device operates.

Vibrating the hospital pole is undesired. Vibration caused by the medical device upon the hospital pole 14 could create adverse effects to other medical devices on the hospital pole. For example and not limited, vibration could adversely effect the administration and dosage of medication delivered to a patient. If a patient is receiving medicine intravenously, the patient is normally receiving the medicine through a bag. That bag is positioned on the hospital pole 14 and the bag is interconnected to the patient through an IV line. The amount of medicine that traverses through the IV line is controlled by a valve like device. Obviously, if the valve is vibrated, the valve may be adjusted and result in the misadministration of medicine, which could be deleterious. That means vibration on a hospital pole 14 is to be kept to a minimum to inhibit such adverse effects.

The current interconnection system decreases the vibrational effects on hospital poles 14, which is not possible with the current hospital pole clamping systems.

The present invention's clamp system 12 has a first clamp member 12a and a second clamp member 12b. Both clamp members are identical except each clamp member 12a,b is positioned on opposite sides of the first trench area 30a. The clamping members 12a,b are also positioned to confront each other.

Each clamping member 12a,b has a biasing apparatus (only the biasing pivot point 50 is shown), and an engagement portion 40—sometimes collectively referred to as a spring loaded cam device. Each biasing apparatus 50 urges the respective engagement member 40 of clamping members 12a,b toward the other engagement member 40. That position is referred to as the preferred position. In the preferred position, biasing apparatus positions the engagement portion 40 of each clamping member 12a,b to inhibit the hospital pole 14 from entering into the pole receiving/alignment trench 30.

The engagement members 40 of clamping members 12a,b do not contact each other as illustrated in FIG. 1—and this is the preferred embodiment. In alternative embodiments the clamping members 12a,b may contact each other in the preferred position. If the clamping members 12a,b do contact each other, the contact should minimally contact each other. Whichever embodiment is utilized, the engagement members 40 extend toward each other in the preferred position.

The engagement member 40 has a receiving exterior surface 42 and an attachment exterior surface 44. The receiving exterior surface 42 is designed to allow a hospital pole 14 to be positioned against it prior to entering the entire first trench area 30a. When the hospital pole 14 is positioned against the receiving exterior surface 42, a person raises the case 10 in relation to the pole 14. While the case 10 is being raised in relation to the pole 14, each engagement portion 40 of clamping members 12a,b rotates about the biasing pivot point 50 toward the case's bottom 34.

When the receiving exterior surface 42 rotates toward the bottom 34, the receiving exterior surface 42 eventually does not inhibit the first trench area 30a from receiving the hospital pole 14. That position is referred to as the maximum tension position because the biasing apparatus is attempting to have the engagement portion revert to the preferred position as soon as possible.

The hospital pole 14 enters the first trench area 30a while the engagement portions 40 are in the maximum tension position and the second trench area 30b. While the engagement members are in the maximum tension position, the respective biasing apparatus of clamping members 12a,b attempt to revert the respective engagement member toward the preferred position. The engagement members are unable to revert to the preferred position because the pole 14 inhibits that reversion. Instead the engagement members are positioned at the attachment position. The attachment position is obtained when the biasing apparatus attempts to revert the engagement members to the preferred position but the attachment exterior surface 44 contacts the hospital pole 14 and applies sufficient pressure to the hospital pole 14, as illustrated in FIG. 2, to secure the case 10 and the corresponding medical instrument device to the hospital pole 14.

In one embodiment, the attachment exterior surface 44 has a plurality of ribs 45. The ribs increase the number of distinct areas that the attachment exterior surface 44 contacts the hospital pole 14. The increased contact areas decrease the chance of the attachment exterior surface 44 losing contact with the hospital pole 14.

To further increase the attachment capabilities of the attachment exterior surface 44 to the hospital pole 14, the hospital pole can have circumferential bands of rubber 87 that grip the pole 14 at the location of where the attachment exterior surface 44 is supposed to contact the hospital pole 14. The circumferential bands of rubber 87 can also be located on the pole area that contacts the second trench area 30b. The circumferential bands of rubber 87 increase the attachment properties of the attachment exterior surface 44 and the hospital pole 14.

The biasing apparatus applies a force to the hospital pole 14 through the attachment exterior surface 44 that is equal to or preferably greater than the gravitational force applied to the case 10 and the corresponding medical instrument device. By default the case 10 is lowered (preferably slightly) in relation to the hospital pole 14 to ensure the biasing apparatus through the attachment exterior surface 44 applies the maximum force against the hospital pole 14. To obtain the maximum force, the engagement member 40 is made of a material that retains its overall shape, like a hard polymeric material, and simultaneously has a portion of the engagement member reversibly conform to a portion of the hospital pole, a.k.a., IV pole, shape.

Removing the case 10 from the hospital pole 14 is just the reverse process for attaching the case 10 to the hospital pole 14. When released from the pole, the engagement member 40 reverts to its original shape.

When used, the hospital pole is positioned near a support surface that contains a patient. The support surface can be a hospital bed, an operating table, a wheelchair or any device that a patient is positioned thereon.

The clamp system 12 also decreases the medical device's vibrational effects on the hospital pole. The clamp system 12 through the engagement members and the corresponding biasing apparatuses allows the medical device to have minimal movement without detaching from the hospital pole and simultaneously absorb some of the vibrational effect that should be transferred to the hospital pole. Since the clamp system absorbs at least a portion of the vibrational effect, the clamp system decreases the device's vibrational effect on the hospital pole 14

Whereas the present invention has been described with respect to a specific embodiment thereof, it will be understood that various changes and modifications will be suggested to one skilled in the art and it is intended to encompass such changes and modifications as fall within the scope of the appended claims.

We claim:

1. A medical instrument device comprising:
a medical instrument to benefit a patient positioned on a support surface and the medical instrument is contained in a case;
the case having at least one surface having a hospital pole trench area, wherein the hospital pole trench area is divided into a first trench area and a second trench area and the first trench area is separated from the second trench area by an area that does not contact a hospital pole when the hospital pole is positioned in the hospital pole trench area, and a clamping system;
the clamping system has a first clamping member, a first biasing apparatus, a second clamping member, and a second biasing apparatus affixed to the case;
the first clamping member is positioned on a first side of the hospital pole trench area and the second clamping member is positioned on a second side of the hospital pole trench area, and the first clamping member and the second clamping member are opposed to each other;
the first biasing apparatus positions the first clamping member into a first preferred position and the second biasing apparatus positions the second clamping member into a second preferred position, the first preferred position and the second preferred position inhibit a hospital pole from entering the hospital pole trench area;
the hospital pole enters the hospital pole trench area by
(A) positioning the hospital pole to
(i) align with the hospital pole trench area, and
(ii) contact the first clamping member and the second clamping member,
(B) raising and pushing the medical instrument device in relation to and against the pole so the pole allows the first clamping member and the second clamping member to rotate until the hospital pole trench area is exposed,
(C) sliding the hospital pole into the hospital pole trench area which results in the first and second biasing apparatuses to urge respectively the first clamping member and the second clamping member toward the respective first and second preferred positions, and
(D) lowering the medical instrument device on the hospital pole to obtain
(i) a maximum contact between
(a) the first clamping member and the hospital pole and
(b) the second clamping member and the hospital pole, and
(ii) a maximum force from
(a) the first biasing apparatus through the first clamping member to the hospital pole and
(b) the second biasing apparatus through the second clamping member to the hospital pole;
wherein the maximum force is greater than the weight of the medical instrument device; and
wherein the first clamping member and the second clamping member are positioned at the first trench area.

2. The medical instrument device of claim 1 wherein the first clamping member and the second clamping member have polymeric exterior surfaces.

3. The medical instrument device of claim 1 wherein the first clamping member and the second clamping member have ribs on the exterior surfaces.

4. The medical instrument device of claim 1 wherein the clamping member has a receiving exterior surface and an attachment exterior surface, wherein the receiving exterior surface is the surface that the hospital pole contacts in step (A) and moves in step (B) and the attachment exterior surface is the surface that the hospital pole contacts in step (D).

5. The medical instrument device of claim 1 wherein the medical instrument device is selected from the group consisting of an intravenous fluid pump, an intravenous fluid gravity controller, an intravenous fluid temperature controller, a blower for a conductive blanket, and a blower for a convective blanket.

6. The medical instrument device of claim 1 wherein the hospital pole has circumferential bands of rubber where the first clamping member and the second clamping member contact the hospital pole.

7. The medical instrument device of claim 1 wherein the hospital pole has circumferential bands of rubber where the second trench area contacts the hospital pole.

8. A medical blower comprising:
a medical blower that pushes a fluid having a predetermined temperature into a cavity of a blanket positioned over or under a patient and the blower has an exterior surface;
the blower's exterior surface has a hospital pole trench area and a clamping system;
the clamping system has a first clamping member, a first biasing apparatus, a second clamping member, and a second biasing apparatus affixed to the blower's exterior surface;
the first clamping member is positioned on a first side of the hospital pole trench area and the second clamping member is positioned on a second side of the hospital pole trench area, and the first clamping member and the second clamping member are opposed to each other;
the first biasing apparatus positions the first clamping member into a first preferred position and the second biasing apparatus positions the second clamping member into a second preferred position, the first preferred position and the second preferred position inhibit a hospital pole from entering the hospital pole trench area;
the hospital pole enters the hospital pole trench area by
(A) positioning the hospital pole to
(i) align with the hospital pole trench area, and
(ii) contact the first clamping member and the second clamping member,
(B) raising and pushing the medical instrument device in relation to and against the pole so the pole allows the first clamping member and the second clamping member to rotate until the hospital pole trench area is exposed,
(C) sliding the hospital pole into the hospital pole trench area which results in the first and second biasing apparatuses to urge respectively the first clamping member and the second clamping member toward the respective first and second preferred positions, and
(D) lowering the blower on the hospital pole to obtain (i) a maximum contact between
(a) the first clamping member and the hospital pole and
(b) the second clamping member and the hospital pole, and
(ii) a maximum force from
(a) the first biasing apparatus through the first clamping member to the hospital pole and
(b) the second biasing apparatus through the second clamping member to the hospital pole;
wherein the maximum force is greater than the weight of the blower; and
wherein the hospital pole has circumferential bands of rubber where the first clamping member and the second clamping member contact the hospital pole.

9. The medical blower of claim 8 wherein the first clamping member and the second clamping member have polymeric exterior surfaces.

10. The medical blower of claim 8 wherein the first clamping member and the second clamping member have ribs on the exterior surfaces.

11. The medical blower of claim 8 wherein the clamping member has a receiving exterior surface and an attachment exterior surface, wherein the receiving exterior surface is the surface that the hospital pole contacts in step (A) and moves in step (B) and the attachment exterior surface is the surface that the hospital pole contacts in step (D).

12. The medical blower of claim 8 wherein the blanket is a convective blanket.

13. The medical blower of claim 8 wherein the blanket is a conductive blanket.

14. The medical blower of claim 8 wherein the fluid is air.

15. The medical blower of claim 8 wherein the fluid is a liquid.

16. The medical blower of claim 8 wherein the hospital pole trench area is divided into a first trench area and a second trench area and the first trench area is separated from the second trench area by an area that does not contact the hospital pole when the hospital pole is positioned in the hospital pole trench area.

17. The medical blower of claim 16 wherein the first clamping member and the second clamping member are positioned at the first trench area, 18. The medical blower of claim 17 the hospital pole has circumferential bands of rubber where the second trench area contacts the hospital pole.

* * * * *